(12) United States Patent  (10) Patent No.: US 9,161,829 B2
Dolan  (45) Date of Patent: Oct. 20, 2015

(54) IMPLANTABLE MEDICAL DEVICE AND METHODS OF DELIVERING THE IMPLANTABLE MEDICAL DEVICE

(71) Applicant: Boston Scientific Scimed, Inc., Maple Grove, MN (US)

(72) Inventor: Andrew Dolan, Bridgewater, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 163 days.

(21) Appl. No.: 13/864,847

(22) Filed: Apr. 17, 2013

(65) Prior Publication Data

US 2013/0281768 A1  Oct. 24, 2013

Related U.S. Application Data

(60) Provisional application No. 61/636,213, filed on Apr. 20, 2012.

(51) Int. Cl.
*A61F 2/00* (2006.01)
*A61F 13/00* (2006.01)

(52) U.S. Cl.
CPC .................... *A61F 2/0045* (2013.01)

(58) Field of Classification Search
CPC ..... A61F 2/0036; A61F 2/005; A61F 2/0009; A61F 2/04; A61F 6/08; A61F 2250/0007; A61F 2250/0031; A61F 2002/047; A61F 2/004; A61F 2017/00805
USPC .......................... 600/37, 29–32; 128/834, 885
See application file for complete search history.

(56) References Cited

U.S. PATENT DOCUMENTS

| 2002/0028980 | A1* | 3/2002 | Thierfelder et al. | 600/37 |
| 2006/0195007 | A1* | 8/2006 | Anderson et al. | 600/29 |
| 2009/0318752 | A1* | 12/2009 | Evans et al. | 600/37 |
| 2010/0261955 | A1* | 10/2010 | O'Hern et al. | 600/37 |
| 2010/0305394 | A1 | 12/2010 | Rosenblatt | |

(Continued)

FOREIGN PATENT DOCUMENTS

WO  2013/158875 A1  10/2013

OTHER PUBLICATIONS

International Search Report for PCT Patent Application No. PCT/US2013/037160, mailed on Aug. 7, 2013, 11 pages.

(Continued)

*Primary Examiner* — Christine H Matthews
*Assistant Examiner* — Sunita Reddy
(74) *Attorney, Agent, or Firm* — Brake Hughes Bellermann LLP (57) ABSTRACT

In one general aspect, a medical device can include a first elongate member made of a material and having a proximal end portion configured to be attached to a first portion of a bodily portion within a body of a patient where the first elongate member has a distal end portion. The medical device can include a second elongate member made of the material and having a proximal end portion configured to be attached to a second portion of the bodily portion where the first elongate member has a distal end portion. The medical device can also include a third elongate member having a proximal end portion in contact with and coupled to the distal end portion of the first elongate member and in contact with and coupled to the distal end portion of the second elongate member.

20 Claims, 9 Drawing Sheets

(56) References Cited

U.S. PATENT DOCUMENTS

| | | | |
|---|---|---|---|
| 2011/0301407 A1* | 12/2011 | Deitch | 600/30 |
| 2012/0108894 A1* | 5/2012 | Young et al. | 600/37 |
| 2013/0061855 A1* | 3/2013 | Fairneny et al. | 128/834 |
| 2013/0317286 A1* | 11/2013 | Bluecher et al. | 600/37 |

OTHER PUBLICATIONS

International Preliminary Report on Patentability for PCT Patent Application No. PCT/US2013/037160, mailed on Oct. 30, 2014, 8 pages.

* cited by examiner

IMPLANTABLE MEDICAL DEVICE AND METHODS OF DELIVERING THE IMPLANTABLE MEDICAL DEVICE

CROSS-REFERENCE TO RELATED APPLICATION

This application is a Nonprovisional of, and claims priority to, U.S. Patent Application No. 61/636,213, filed on Apr. 20, 2012, entitled "IMPLANTABLE MEDICAL DEVICE AND METHODS OF DELIVERING THE IMPLANTABLE MEDICAL DEVICE", which is incorporated by reference herein in its entirety.

TECHNICAL FIELD

The embodiments herein generally relate to medical devices and procedures, particularly devices configured to be delivered and placed into a patient's body for treatment of pelvic organ prolapse.

BACKGROUND

Genital prolapse or pelvic organ prolapse is the protrusion of the pelvic organs into or out of the vaginal canal. Pelvic floor prolapse affects many women in the U.S. and almost all of them undergo at least one reconstructive pelvic surgery in their lifetime. Many of the cases may be the result of damage to the vaginal and pelvic support tissue by stretching or tearing of the connective tissue within the pelvic space due to childbirth, age, obesity, post-menopausal conditions or chronically elevated intra-abdominal pressure. The results are the distention of organs such as the bladder and rectum, into the vagina, as well as various stages of vaginal avulsion.

Surgical therapy/technique is usually performed for the treatment of pelvic organ prolapse. These techniques for prolapse treatment include plication of the torn connective tissues and re-suspension of the vagina/uterus. Some traditional suspension techniques include utero-sacral suspension and sacrospinus ligament suspension. Some procedures for vaginal suspension include sacrocolpopexy, where the vagina/uterus is suspended to the sacral promontory with an implanted graft material. Some of the grafts have demonstrated improved long-term success of the repair.

Y-shaped meshes may be used as a graft to treat vaginal vault prolapse. The Y-shaped mesh aids vaginal cuff suspension to the sacrum and may provides long-term support. The procedure can be minimally invasive (such as via a Laparoscopic Sacral Colpopexy) or traditional (such as via an open sacral colpopexy). These Y-shaped meshes may be made of various types of polymeric or biological materials. Various doctors/operators may prefer a particular type of implant to repair the pelvic damage depending on the surgical requirements and a patient's history. Some doctors/operators may choose a biologic graft over a synthetic polypropylene graft as the biologic graft minimizes erosion as opposed to synthetic meshes. Others may prefer synthetic grafts as they may provide long-term reinforcement for support structures. The existing implants are available either as a biologic graft or polypropylene graft. These implants do not include both a polypropylene and a biological material for specific usage to specific anatomical locations.

Thus, there is a need for an improved polypropylene medical device/implant having biological material at specific locations to suit the anatomical structure.

SUMMARY

In one general aspect, a medical device can include a first elongate member made of a material and having a proximal end portion configured to be attached to a first portion of a bodily portion within a body of a patient where the first elongate member has a distal end portion. The medical device can include a second elongate member made of the material and having a proximal end portion configured to be attached to a second portion of the bodily portion where the first elongate member has a distal end portion. The medical device can also include a third elongate member having a proximal end portion in contact with and coupled to the distal end portion of the first elongate member and in contact with and coupled to the distal end portion of the second elongate member.

DETAILED DESCRIPTION

In general, the embodiments disclosed herein are directed to systems, methods, and devices for treating vaginal prolapse. However, the embodiments may be equally employed for other treatment purposes such as pelvic organ prolapse. As described below in various illustrative embodiments, the embodiments provide systems, methods, and devices employing an improved medical device configured to be implanted within a patient's body to support pelvic organs for the treatment of pelvic prolapse.

The term patient may be used hereafter for a person who benefits from the medical device or the methods disclosed in the presented embodiments. For example, the patient may be a person whose body receives the medical device disclosed by the present embodiments in a surgical treatment. For example, in some embodiments, the patient may be a human female, a human male, or any other mammal.

Figure 1:
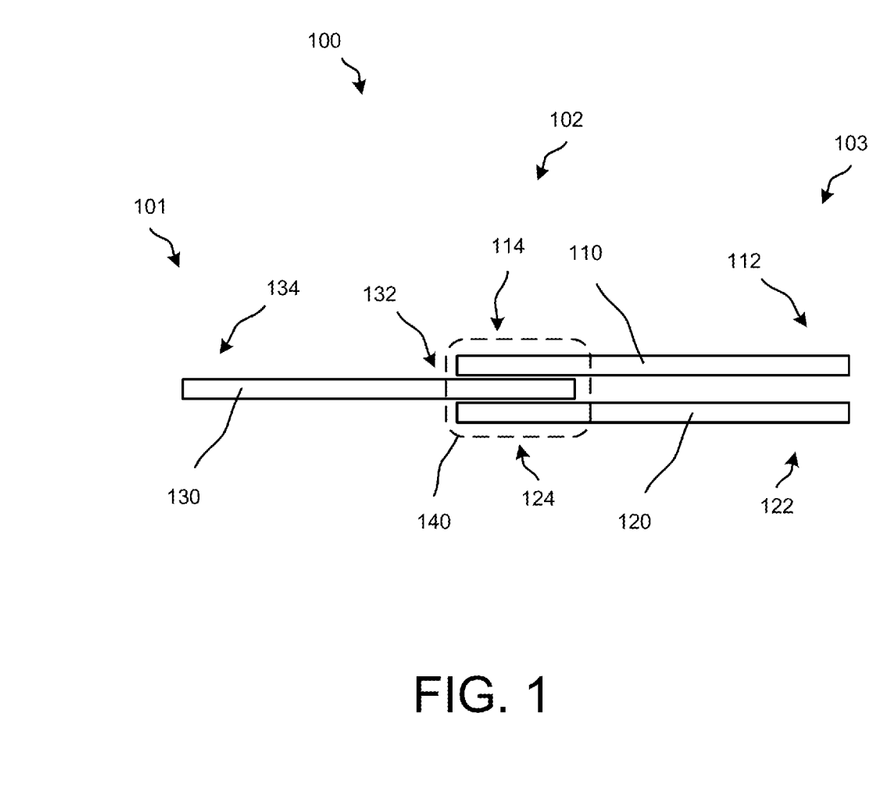
FIG. 1 is a schematic block diagram of a medical device configured to be implanted within a body of a patient.

FIG. 1 is a schematic block diagram of a medical device 100 configured to be implanted within a body of a patient. In some embodiments, the medical device 100 is a bodily implant configured to support bodily tissues for the treatment of pelvic floor prolapse. For example, the medical device 100 can be used, during a medical procedure, to treat various female pelvic dysfunctions, including procedures to treat urinary incontinence, and correcting various prolapse conditions such as uterine prolapse, cystoceles, rectoceles, and vaginal vault prolapse.

As shown in FIG. 1, the medical device 100 includes a first elongate member 110, a second elongate member 120, and a third elongate member 130. The first elongate member 110 has a proximal end portion 112 and a distal end portion 114, and the second elongate member 120 has a proximal end portion 122 and a distal end portion 124. The third elongate member 130 has a distal end portion 134, and a proximal end portion 132 disposed between the distal end portion 114 of the first elongate member 110 and the distal end portion 124 of the second elongate member 120. The proximal end portion 132 of the third elongate member 130, the distal end portion 114 of the first elongate member 110 and the distal end portion 124 of the second elongate member 120 collectively define a layered portion 140 of the medical device 100. In some embodiments, the layered portion 140 can be referred to as a multi-layered portion. In this embodiment, the layered portion 140 includes exactly three layers. In some embodiments, the layered portion 140 can include more than three layers or less than three layers.

As shown in FIG. 1, the layered portion 140 of the medical device 100 is included in or disposed at a medial portion 102 of the medical device 100. The distal end portion 134 of the third elongate member 130 is included in or disposed at a distal portion 101 of the medical device 100. Accordingly, the third elongate member 130 extends distally from the layered portion 140 to the distal portion 101 of the medical device 100. The proximal end portion 112 of the first elongate member 110 and the proximal end portion 122 of the second elongate member 120 are included in or disposed at a proximal portion 103 of the medical device 100. Accordingly, the proximal end portion 112 of the first elongate member 110 extends proximally from the layered portion 140 to the proximal portion 103 of the medical device. Also, the proximal end portion 122 of the second elongate member 120 extends proximally from the layered portion 140 to the proximal portion 103 of the medical device.

The elongate members 110, 120, 130 are configured to be coupled to (e.g., attached to, sutured to) bodily portions (e.g., different portions of bodily portions, different sides of bodily portions) within a body of the patient during a medical procedure. For example, during a medical procedure the first elongate member 110 can be attached to a first bodily portion, the second elongate member 120 can be attached to a second bodily portion, and the third elongate member 130 can be attached to a third bodily portion. In some embodiments, the first bodily portion is an exterior surface of an anterior vaginal wall and the second bodily portion is an exterior surface of a posterior vaginal wall of a patient. In some embodiments, the third bodily portion is a sacrum of the patient. Therefore, in some embodiments, the proximal end portion 112 of the first elongate member 110 is attached to the exterior surface (or side) of an anterior vaginal wall and the proximal end portion 122 of the second elongate member 120 is attached to the exterior surface (or side) of a posterior vaginal wall. Also, in such embodiments, the distal end portion 134 of third elongate member 130 is configured to be attached to the sacrum (and/or a tissue proximate to the sacrum).

In some embodiments, the first elongate member 110, the second elongate member 120, and/or the third elongate member 130 are made of a biologic material such as an Allograft and/or a Xenograft. In some embodiments, the biologic material can include cadaveric tissue, bovine dermis, porcine dermis, porcine intestinal sub mucosa, bovine pericardium, a cellulose based product, cadaveric dermis, and/or so forth. In some embodiments, the Allograft materials can include Tutoplast®, Repliform®, DuraDerm®, Urogen®, and/or so forth. In some embodiments, the Xenograft materials can include Xenoform® (e.g., Xenoform Matrix), Stratisis®, Dermatrix® and/or so forth. In some embodiments, the first elongate member 110, the second elongate member 120, and/or the third elongate member 130 can be made of a biologic material because the biologic material can be relatively robust against tissue erosion. Unlike some materials, the biologic material may not grow into a tissue in an undesirable fashion (e.g., may not grow through a vaginal wall to which the elongate member is attached).

In some embodiments, the first elongate member 110, the second elongate member 120, and/or the third elongate member 130 are made of a synthetic material such as a polymeric mesh body, a polymeric planar body without mesh cells and structures, and/or so forth. In some embodiments, the synthetic material can include polypropylene, polyester, polyethylene, nylon, PVC, polystyrene, and/or so forth. In some embodiments, a mesh body of the synthetic material can be made of a non-woven polymeric material. In some embodiments, the synthetic material can include a Polyform® Synthetic Mesh developed by the Boston Scientific Corporation. The Polyform® Synthetic Mesh can be made from uncoated monofilament macro-porous polypropylene. If made of a synthetic material such as a mesh, the mesh can have a specified weight. In some embodiments, the mesh weight can be approximately between 15 g/cm$^2$ to 35 g/cm$^2$ (e.g., 20 g/cm$^2$, 25 g/cm$^2$, 30 g/cm$^2$). In some embodiments, the first elongate member 110, the second elongate member 120, and/or the third elongate member 130 can be made of a synthetic material because the synthetic material can have a relatively high strength that can support a bodily portion (e.g., a vaginal apex from attachment at a sacrum) without deforming (e.g., sagging, stretching) over time in an undesirable fashion compared with other materials.

As a specific example, the first elongate member 110 and the second elongate member 120 of the medical device 100 can be made of a xenograft material. The third elongate member 130 of the medical device 100 can be made of a synthetic polypropylene material. As another specific example, all of the first elongate member 110, the second elongate member 120, and the third elongate member 130 of the medical device 100 can be made of a xenograft material. Because the elongate members 110, 120, and 130 can be made of different materials, the layered portion 140 can also include a combination of materials. For example, if the elongate member 130 is made of a synthetic material and the elongate members 110, 120 are made of biologic material, the layered portion 140 can include a biologic-synthetic-biologic layered structure. In such embodiments, the biologic material of the first elongate member 110 and the second elongate member 120 can have desirable properties that are robust against tissue erosion to a vaginal wall where they can be attached, and the synthetic material of the third elongate member 130 can provide a desirable level of support between a vagina and a sacrum where the distal end portion 134 of the third elongate member 130 can be attached. In some embodiments, the layered portion 140 (listed from the top layer to the bottom layer) can include a synthetic-synthetic-biologic layered structure, a synthetic-biologic-synthetic layered structure, a biologic-biologic-synthetic layered structure, and so forth.

In some embodiments, the first elongate member 110, the second elongate member 120, and/or the third elongate member 130 are manufactured with a smooth surface (e.g., a relatively smooth surface) to avoid/reduce irritation on body tissues (e.g., adjacent body tissues) of a patient when placing (e.g., implanting) the medical device 100 during a medical procedure and/or after the medical device 100 has been placed (e.g., implanted). In some embodiments, the first elongate member 110, the second elongate member 120, and/or the third elongate member 130 is made of a flexible (e.g., stretchable, malleable) material configured to adapt movements along the anatomy of the human body and/or to reduce suture pullout. In some embodiments, the first elongate member 110, the second elongate member 120, and/or the third elongate member 130 can be manufactured with a specified softness, lightness, conformity, mesh weight, and/or strength for efficient tissue repair and implantation in a desirable fashion.

In some embodiments, one or more of the elongate members 110, 120, and 130 can be configured with a predefined shape for coupling to a specific anatomical feature within a body of a patient. In some embodiments, the predefined shape can be sufficiently flexible for reshaping during a medical procedure. In some embodiments, one or more of the elongate members 110, 120, and 130 can be made of a flexible (e.g., malleable) material so that a surgeon/operator can mold the second portion to a shape (or profile) of a specific anatomical feature (e.g., a vaginal vault).

In this embodiment, the proximal end portion 132 of the third elongate member 130 is coupled to the distal end portion 114 of the first elongate member 110 and is coupled to the distal end portion 124 of the second elongate member 120. In some embodiments, the proximal end portion 132 of the third elongate member 130 can be coupled to the distal end portion 114 of the first elongate member 110 and/or coupled to the distal end portion 124 the second elongate member 120 using attachment elements including a suture, an adhesive, a bonding agent, a mechanical fastener (e.g., a clip (e.g., a medical grade plastic clip, a medical grade metal clip), a pin, a clamp, a rivet, an anchor), and/or so forth. In some embodiments, the sutures may be made of biological materials and/or synthetic materials. In some embodiments, the proximal end portion 132 of the third elongate member 130 can be removably coupled or fixedly coupled to the distal end portion 114 of the first elongate member 110. In some embodiments, the proximal end portion 132 of the third elongate member 130 can be removably coupled or fixedly coupled to the distal end portion 124 the second elongate member 120 using one or more attachment elements.

As a specific example, the proximal end portion 132 of the third elongate member 130, the distal end portion 114 the first elongate member 110, and the distal end portion 124 second elongate member 120 can be fixedly coupled together using a set of sutures into the layered portion 140. The set of sutures can be configured with a strength (e.g., a thickness, a tensile strength) for fixedly binding these components to form the layered portion 140 while having a flexibility for being knotted.

Figure 2:
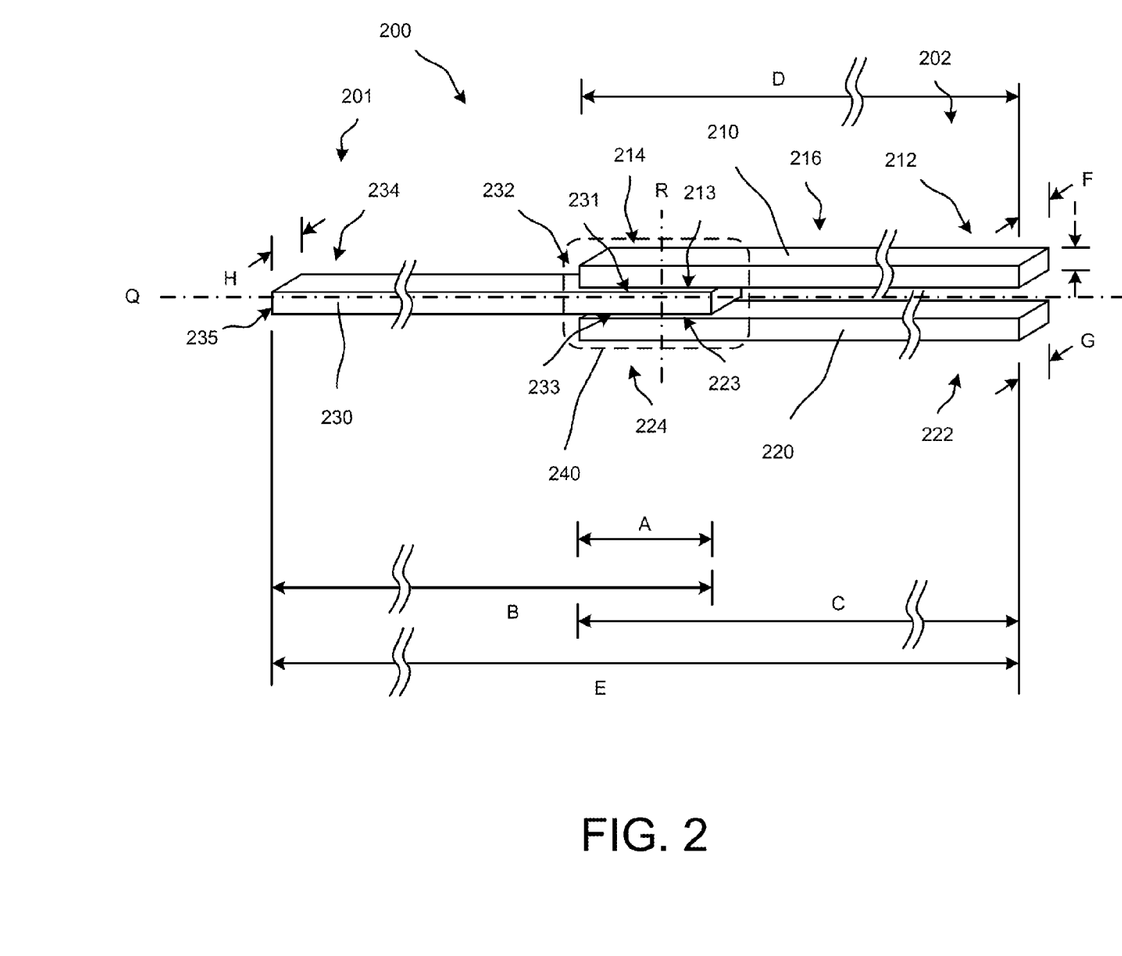
FIG. 2 is a schematic diagram of a perspective view of a medical device configured to be implanted within a body of a patient.

FIG. 2 is a schematic diagram of a perspective view of a medical device 200 configured to be implanted within a body of a patient. In some embodiments, the medical device 200 is a bodily implant configured to support bodily tissues for the treatment of pelvic floor prolapse. As shown in FIG. 2, the medical device 200 includes a first elongate member 210, a second elongate member 220, and a third elongate member 230. The first elongate member 210 has a proximal end portion 212 and a distal end portion 214, and the second elongate member 220 has a proximal end portion 222 and a distal end portion 224. The third elongate member 230 has a distal end portion 234, and has a proximal end portion 232 disposed between the distal end portion 214 of the first elongate member 210 and the distal end portion 224 of the second elongate member 220. The distal end portion 234 can have a distal edge 235 on a distal portion 201 of the medical device 200 that is opposite the proximal portion 202 of the medical device 200.

As shown in FIG. 2, medical device 200 includes a layered portion 240 formed with (e.g., defined by) the proximal end portion 232 of the third elongate member 230, the distal end portion 214 of the first elongate member 210, and the distal end portion 224 of the second elongate member 220. Specifically, a surface 231 of the proximal end portion 232 of the third elongate member 230 is coupled to a surface 213 (also can be referred to as an interior surface or as an inward facing surface) of the distal end portion 214 of the first elongate member 210. Also, a surface 233 of the proximal end portion 232 of the third elongate member 230 is coupled to a surface 223 (also can be referred to as an interior surface or as an inward facing surface) of the distal end portion 224 of the second elongate member 220. The surface 231 can be referred to as being on one side of the proximal end portion 232 of the third elongate member 230 and the surface 233 can be referred to as being on another side of the proximal end portion 232 of the third elongate member 230.

In some embodiments, one or more of the surfaces 213, 223, 231, and 233 can be substantially flat and/or flexible surfaces. In some embodiments, one or more of the surfaces 213, 223, 231, and 233 can be referred to as planar surfaces. Accordingly, in this embodiment, the surfaces 213, 223, 231, and 233 are substantially parallel to one another. In other words, each of the surfaces 213, 223, 231, and 233 are substantially aligned along parallel planes (or surfaces (e.g., curved surfaces)). As shown in FIG. 2, each of the surfaces 213, 223, 231, and 233 are substantially aligned along a plane orthogonal to (or substantially orthogonal to) axis R. The axis R is orthogonal to (or substantially orthogonal to) longitudinal axis Q, along which the medical device 200 and elongate members 210, 220, and 230 are aligned.

As shown in FIG. 2, the first elongate member 210 has a length D and a width F that is substantially the same as a length C and a width G, respectively, of the second elongate member 220. In some embodiments, the length D of the first elongate member 210 can be different than (e.g., greater than, less than) the length C of the second elongate member 220. In some embodiments, the width F of the first elongate member 210 can be different than (e.g., greater than, less than) the width G of the second elongate member 220.

Also, as shown in FIG. 2, the third elongate member 230 has a length B and a width H that is substantially the same as the length D and a width F, respectively, of the first elongate member 210 and that is substantially the same as the length C and a width G, respectively, of the second elongate member 220. In some embodiments, the length B of the third elongate member 230 can be different than (e.g., greater than, less than) the length D of the first elongate member 210 and/or the length C of the second elongate member 220. In some embodiments, the width H of the third elongate member 230 can be different than (e.g., greater than, less than) the width F of the first elongate member 210 and/or the width G of the second elongate member 220. In some embodiments, the width F, the width G, and/or the width H of the medical device 200 can be approximately 5 centimeters (cm). In some embodiments, the width F, the width G, and/or the width H of the medical device 200 can be greater than 5 cm (e.g., 7 cm, 10 cm, 12 cm) or can be less than 5 cm (e.g., 4 cm, 3 cm, 1 cm, 0.5 cm).

In some embodiments, the length D of the first elongate member 210, the length C of the second elongate member 220, and/or the length B of the third elongate member 230 can be greater than or less than half of the length E (which can be referred to as an overall length) of the medical device 200. In some embodiments, the length D of the first elongate member 210, the length C of the second elongate member 220, and/or the length B of the third elongate member 230 can be equal to half of the length E of the medical device 200. In some embodiments, the length E of the third elongate member 230 can be defined so that the third elongate member 230 can extend between, for example, a vaginal apex and a sacrum of a patient (or another support location). Also, the length D of the first elongate member 210 and/or the length C of the second elongate member 220 can be defined so that the first elongate member 210 and/or the second elongate member 220 can extend substantially along an entire vaginal wall (e.g., posterior vaginal wall, anterior vaginal wall) of a patient. Specifically, in some embodiments, the length E of the medical device 200 can be approximately 27 centimeters (cm), which can be approximately the distance between a portion of a vaginal wall and a sacrum of a patient (or another support location). In some embodiments, the length E of the medical device 200 can be greater than 27 cm (e.g., 30 cm, 35 cm, 40 cm) or can be shorter than 27 cm (e.g., 25 cm, 20 cm, 15 cm).

As shown in FIG. 2, the width F of the first elongate member 210, the width G of the second elongate member, and the width H of the third elongate member 230 are substantially uniform (along their respective lengths). In this embodiment, all of the elongate members 210, 220, and 230 are rectangular strips that each have a length substantially longer than their respective widths.

In some embodiments, one or more of the elongate members 210, 220, and 230 may have shapes other than those shown in FIG. 2. In some embodiments, the width F of the first elongate member 210, the width G of the second elongate member, and/or the width H of the third elongate member 230 may be non-uniform. For example, one or more of the elongate members 210, 220, and 230 can have a tapered shape, a triangular shape, an hour-glass shape, and/or so forth. As a specific example, the width F of the second elongate member 210, in some embodiments, can vary from the proximal end portion 212 to the distal end portion 214. As another example, although not shown in FIG. 2, the width F of the first elongate member 210 can be different than the width H of the third elongate member 230. In such embodiments, the width of the surface 213 and the width of the surface 231 can be different within the layered portion 240 of the medical device 200. As another example, although not shown in FIG. 2, the width F of the first elongate member 210 can vary along the length D. As a specific example, the first elongate member 210 can have a first width at the proximal end portion 212 and a second width, different from the first width, at the distal end portion 214. In such embodiments, the width of a medial portion 216 of the first elongate member 210 can be the same as, or different from (e.g., greater than, less than), the first width and/or the second width. In some embodiments, the second elongate member 220 and/or the third elongate member 230 can similarly have varying widths along their respective lengths. In some embodiments, the medial portion 216 can have a rectangular shape.

In this embodiment, the layered portion 240 has a length A. Specifically, the distal end portion 214 of the first elongate member 210 has a portion with length A that is coupled to (e.g., overlaps with) a portion of the proximal end portion 232 of the third elongate member 230 that also has length A. Similarly, the distal end portion 224 of the second elongate member 220 has a portion with length A (e.g., overlaps with) that is coupled to a portion of the proximal end portion 232 of the third elongate member 230 that also has length A.

Figure 3A:
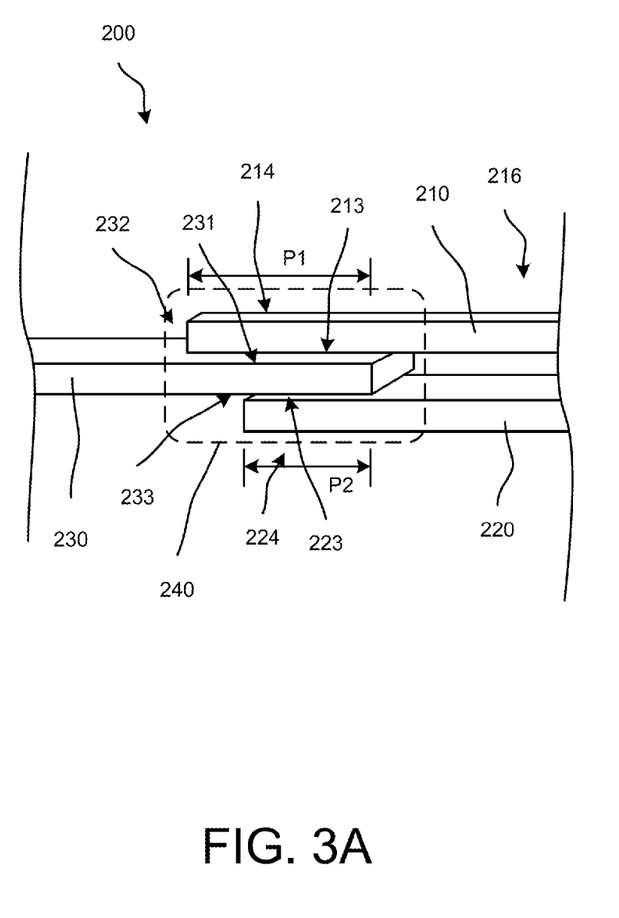
FIG. 3A is a diagram that illustrates the layered portion shown in FIG. 2 modified with different coupled portions between the elongate members.

In some embodiments, the length of the overlapping portion between the first elongate member 210 and the third elongate member 230 can be different than the overlapping portion between the second elongate member 210 and the third elongate member 230. FIG. 3A is a diagram that illustrates the layered portion 240 shown in FIG. 2 modified with different coupled portions between the first elongate member 210, the second elongate member 220, and the third elongate member 230. As shown in FIG. 3A, a length of coupling (e.g., overlap) (shown as dimension P1) between the first elongate member 210 and the third elongate member 230 is different than a length of coupling (e.g., overlap) (shown as dimension P2) between the second elongate member 220 and the third elongate member 230.

Because of the difference in coupling, a surface area of coupling (e.g., overlap) between the first elongate member 210 and the third elongate member 230 and a surface area of coupling (e.g., overlap) between the second elongate member 220 and the third elongate member 230 can be different. The surface area of coupling between the first elongate member 210 and the third elongate member 230 can be defined at least in part by contacting area between the surface 213 of the first elongate member 210 and the surface 231 of the third elongate member 230. Similarly, the surface area of coupling between the second elongate member 220 and the third elongate member 230 can be defined at least in part by contacting area between the surface 223 of the second elongate member 220 and the surface 231 of the third elongate member 230.

In the embodiment shown in FIG. 3A, the width of the third elongate member 230 is approximately the same as the width of the second elongate member 220. However, the width of the first elongate member 210 is smaller than the width of the second elongate member 220 and width of the third elongate member 230. Although not shown in FIG. 3A, the width of the first elongate member 210 and/or the width of the second elongate member 220 can be greater than the width of the third elongate member 230.

Figure 3B:
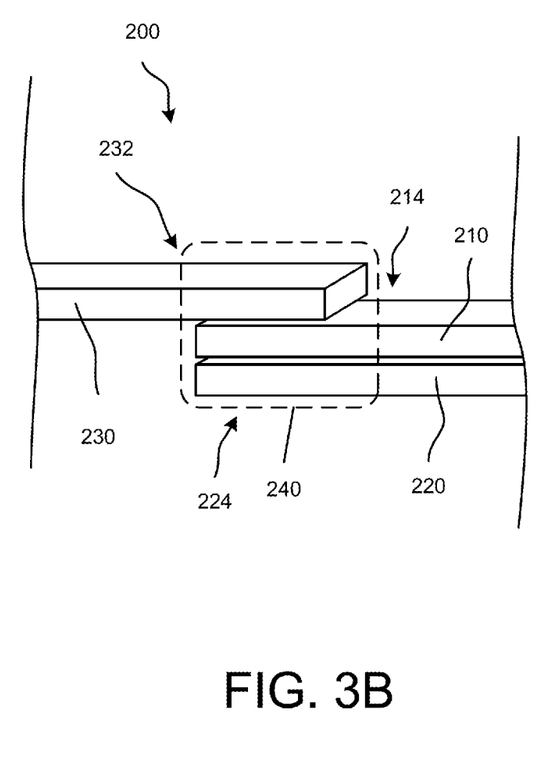
FIG. 3B is another diagram that illustrates the layered portion shown in FIG. 2 modified with different coupled portions between the elongate members.

FIG. 3B is another diagram that illustrates the layered portion 240 shown in FIG. 2 modified with different coupled portions between the first elongate member 210, the second elongate member 220, and the third elongate member 230. In this embodiment, the second elongate member 220 is coupled to the first elongate member 210, which is coupled to the third elongate member 230. Accordingly, in this embodiment, the proximal end portion 232 of the third elongate member 230 is not disposed between the first elongate member 210 and the second elongate member 220, and the third elongate member 230 is separated from (e.g., not directly coupled to) the second elongate member 220. In some embodiments, the configuration shown in FIG. 3B can be combined with one or more of the modifications discussed in connection with FIG. 3A.

Referring back to FIG. 2, each of the elongate members 210, 220, and/or 230 is aligned along the longitudinal axis Q. In some embodiments, one or more of the elongate members 210, 220, and/or 230 may not be aligned along the longitudinal axis Q. For example, the third elongate member 230 can be aligned along the longitudinal axis Q, and the second elongate member 220 can be aligned along an additional axis non-parallel to the longitudinal axis Q. The first elongate member 210 can be aligned along the longitudinal axis Q, the additional axis, or along a different axis non-parallel to the additional axis and the longitudinal axis Q.

In this embodiment, a thickness of each of the elongate members 210, 220, and 230 is uniform. As an illustrative example, the thickness I of the first elongate member 210 as shown in FIG. 2. In some embodiments, the thickness of one or more of the elongate members 210, 220, and/or 230 can be non-uniform. In other words, the thickness of one or more of the elongate members 210, 220, and/or 230 can vary along their respective lengths and/or along their respective widths.

Although not shown in FIG. 2, in some embodiments, one or more of the elongate members 210, 220, and/or 230, can include any combination of biologic material or synthetic material. For example, the distal end portion 214 of the elongate member 210 can be made of a synthetic material, and the medial portion 216 and/or the proximal end portion 212 of the elongate member 210 can be made of a biologic material coupled to the synthetic material. In some embodiments, the first elongate member 210 can be made of a synthetic material, and a pad (or member) made of a biologic material (configured for coupling to a tissue of the patient) can be coupled to the first elongate member 210.

Figure 4A:
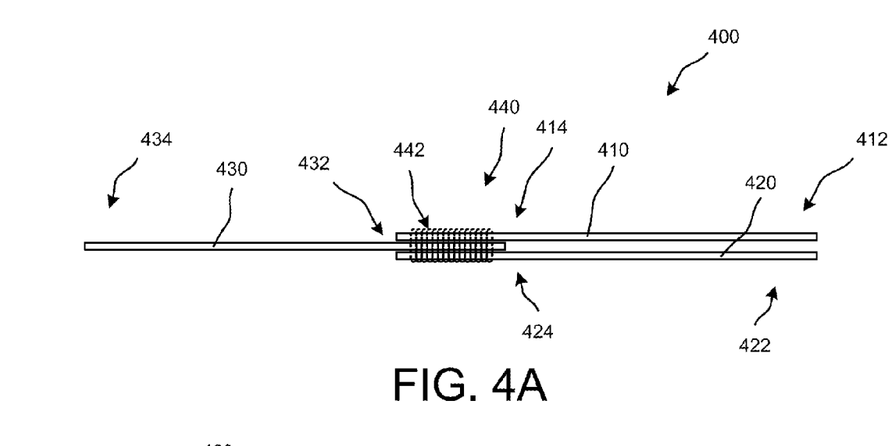
FIG. 4A is a schematic diagram of a side view of a medical device configured to be implanted within a body of a patient.

FIG. 4A is a schematic diagram of a side view of a medical device 400 configured to be implanted within a body of a patient. In some embodiments, the medical device 400 is a bodily implant configured to support bodily tissues for the treatment of pelvic floor prolapse. As shown in FIG. 4A, the medical device 400 includes a first elongate member 410, a second elongate member 420, and a third elongate member 430. The first elongate member 410 has a proximal end portion 412 and a distal end portion 414, and the second elongate member 420 has a proximal end portion 422 and a distal end portion 424. The third elongate member 430 has a distal end portion 434, and a proximal end portion 432 disposed between the distal end portion 414 of the first elongate member 410 and the distal end portion 424 of the second elongate member 420.

As shown in FIG. 4A, medical device 400 includes a layered portion 440 formed with (e.g., defined by) the proximal end portion 432 of the third elongate member 430, the distal end portion 414 of the first elongate member 410, and the distal end portion 424 of the second elongate member 420. In this embodiment, the proximal end portion 422 of the third elongate member 430 is coupled to the distal end portion 414 of the first elongate member 410 and coupled to the distal end portion 424 of the second elongate member 420 via sutures 442 (which are illustrated with dashed lines). In some embodiments, the sutures 442 can be referred to as a set of sutures. The sutures 442 can be configured to fixedly couple the proximal end portion 422 of the third elongate member 430 to the distal end portion 414 of the first elongate member 410 and fixedly couple the proximal end portion 422 of the third elongate member 430 to the distal end portion 424 of the second elongate member 420.

In some embodiments, at least a portion of the sutures 442 can pierce or extend through all three layers included in the layered portion 440. In other words, a single thread in the sutures 442 can pierce or extend through all three layers of elongate members 410, 420, 430 included in the layered portion 440. In some embodiments, one or more of the sutures 442 may pierce or extend through less than all of the layers included in the layered portion 440. For example, a first set of sutures can be configured to couple two layers of the layered portion 440 together including the distal end portion 413 of the first elongate member 410 and the proximal end portion 432 of the third elongate member 430. A second set of sutures can be configured to couple the two layers (which are already coupled using the first set of sutures) of the layered portion 440 to the distal end portion 424 of the second elongate member 420. As mentioned above, in some embodiments, the layered portion 440 of the medical device 400 can be formed by coupling one or more of the elongate members 410, 420, and/or 430 using attachment elements such as adhesives, mechanical fasteners, and/or so forth.

Figure 4B:
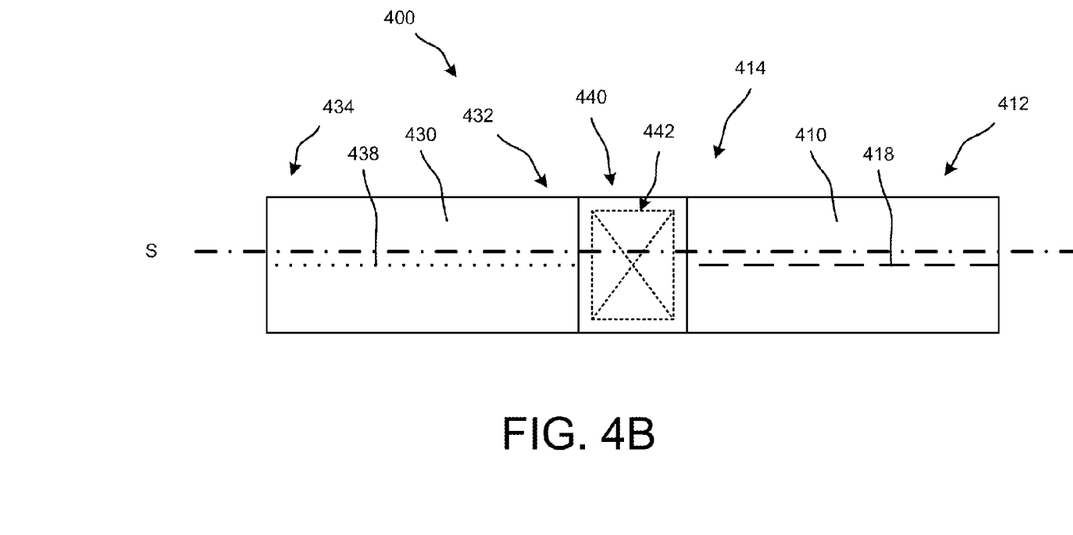
FIG. 4B is a schematic diagram of a top view of the medical device shown in FIG. 4A.

FIG. 4B is a schematic diagram of a top view of the medical device 400 shown in FIG. 4A. As shown in FIG. 4B, the sutures 442 define an X-shape pattern within a rectangular shape. In some embodiments, the sutures 442 can define a different shape and/or pattern than that shown in FIG. 4B. For example, the sutures 442 can define a diamond shape, a Z-shape pattern, a circular shape, an oval-shaped, a vertical crosshatch pattern, a slanted crosshatch pattern, and/or so forth.

As shown in FIG. 4B, the medical device 400 includes several placement features (also can be referred to as implant features or as guidance features) that can be used by, for example, a physician to place (e.g., implant) the medical device 400 within a body of the patient any desirable fashion. In other words, the placement features can be used a visual guide by, for example, a physician to place the medical device 400 within a body of the patient. In this embodiment, the medical device 400 includes a placement feature 438 in the third elongate member 430, and a placement feature 418 in the first elongate member 410. In some embodiments, a placement feature (not shown) may also be included in the second elongate member 420, which is not shown in FIG. 4B. In some embodiments, the medical device 400 may only include a single placement feature. In some embodiments, one or more of the elongate members 410, 420, and/or 430 can include more than one placement feature.

In this embodiment, the placement feature 438 is aligned along a longitudinal axis S of the medical device 400. The placement feature 438, in this embodiment, is centered within (e.g., within the width of) the third elongate member 430, and is defined by a series of holes. In some embodiments, the series of holes or openings defining the placement feature 438 can be different from holes of a mesh that can be used to make the third elongate member 430.

Also, in this embodiment, the placement feature 418 is aligned along the longitudinal axis S of the medical device 400. The placement feature 418, in this embodiment, is centered within (e.g., within the width of) the first elongate member 410, and is defined by a stripe made of a colored thread or coloring agent (e.g., a dye). In some embodiments, the placement feature 418 can be sewn into or coupled to the first elongate member 410.

In some embodiments, one or more placement features included in the medical device 400 can be off-center (with respect to a width) of medical device 400. In some embodiments, one or more placement features may be aligned along an axis that is non-parallel to (e.g., orthogonal to) the longitudinal axis S. In some embodiments, one or more placement features included in the medical device 400 can be made from a variety of materials including mechanical fasteners, ink, sutures, and/or made using a variety of methods including crimping, folding, and/or so forth. In some embodiments, one or more placement features can be nonlinear (e.g., can include curved lines), and/or may be included only along a portion of the length of one or more of the elongate members 410, 420, and/or 430.

Figure 5:
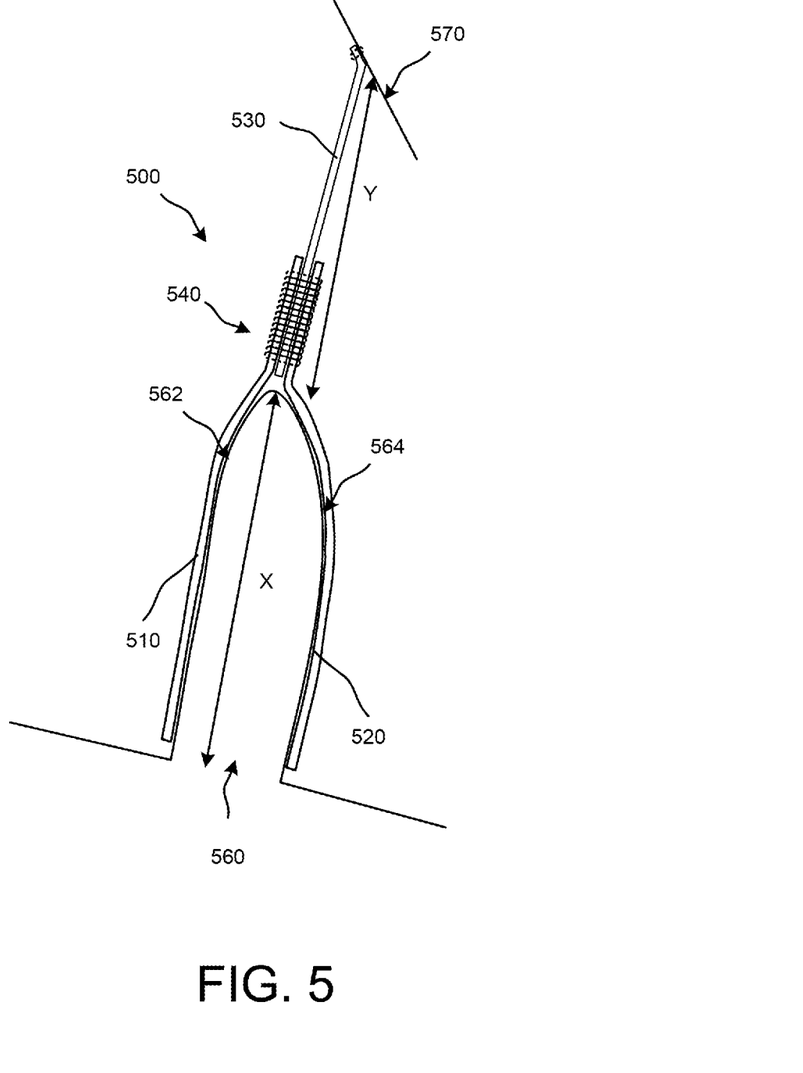
FIG. 5 is a diagram that illustrates placement of a medical device within a body of the patient, according to an embodiment.

FIG. 5 is a diagram that illustrates placement of a medical device 500 within a body of the patient, according to an embodiment. The medical device 500 can include any of the features of the medical devices described previously (e.g., medical device 100 shown in FIG. 1). As shown in FIG. 5, a first elongate member 510 of the medical device 500 is coupled to (e.g., attached to) a first portion 562 of a bodily portion 560 of a patient, and a second elongate member 520 of the medical device 500 is coupled to a second portion 564 of the bodily portion 560 of the patient.

As shown in FIG. 5, a third elongate member 530 is coupled to another bodily portion 570 of the patient. In some embodiments, the third elongate member 530 can be coupled to the bodily portion 570 of the patient via one or more sutures, mechanical fasteners, and/or so forth. In this embodiment, a layered portion 540 of the medical device 500 includes at least a portion of each of the elongate members 510, 520, 530.

In some embodiments, the medical device 500 can be used in a sacrocolpopexy procedure. In such embodiments, the bodily portion 560 can be a vagina of the patient, and the first elongate member 510 and the second elongate member 520 can be disposed around at least a portion of a vaginal apex. The first portion 562 can be an anterior vaginal wall and the second portion 564 can be a posterior vaginal wall. Also, in such embodiments, the bodily portion 570 can be a sacrum of the patient. If the first portion 562 is an anterior vaginal wall, the first elongate member 510 can be referred to as an anterior elongate member. If the second portion 564 is a posterior vaginal wall, the second elongate member 520 can be referred to as a posterior elongate member.

As shown in FIG. 5, the first elongate member 510 and the second elongate member 520 each have a length that is approximately equal to a length X of the bodily portion 560. In some embodiments, the first elongate member 510 and/or the second elongate member 520 can have a length that is shorter than (e.g., less than half than) or longer than the length X of the bodily portion 560. In some embodiments, the first elongate member 510 and/or the second elongate member 520 can each have a length sufficient to address rectocele and cystocele in addition to apical prolapse. In some embodiments, the medical device 500 can be configured to prevent (or substantially prevent) uterine or upper vaginal prolapse by, for example, supporting the apex of the vagina from the sides of the sacrum (also can be referred to as level 1 support). In some embodiments, the medical device 500 can be configured to prevent (or substantially prevent) prolapse of the bladder (i.e., cystocele) and the rectum (i.e., rectocele) into the vagina by, for example, support of the vagina via the pelvic side wall (also can be referred to as level 2 support).

Also, as shown in FIG. 5, the third elongate member 510 has a length that is approximately equal to (or slight longer than) a distance Y between the bodily portion 560 and the bodily portion 570. In some embodiments, the third elongate member 530 can have a length that is shorter than (e.g., less than half than) or longer than the distance Y.

In some embodiments, one or more portions of the medical device 500 can be trimmed by a physician before, or when placing, the medical device 500 within the body of the patient. For example, the third elongate member 530 can be trimmed to a shorter length so that the third elongate member 530 can be attached in a desirable fashion between the bodily portion 560 and the bodily portion 570. Similarly, the first elongate member 510 and/or the second elongate member 520 can be trimmed prior to, or when placing, the medical device 500 within the body of the patient.

Figure 6:
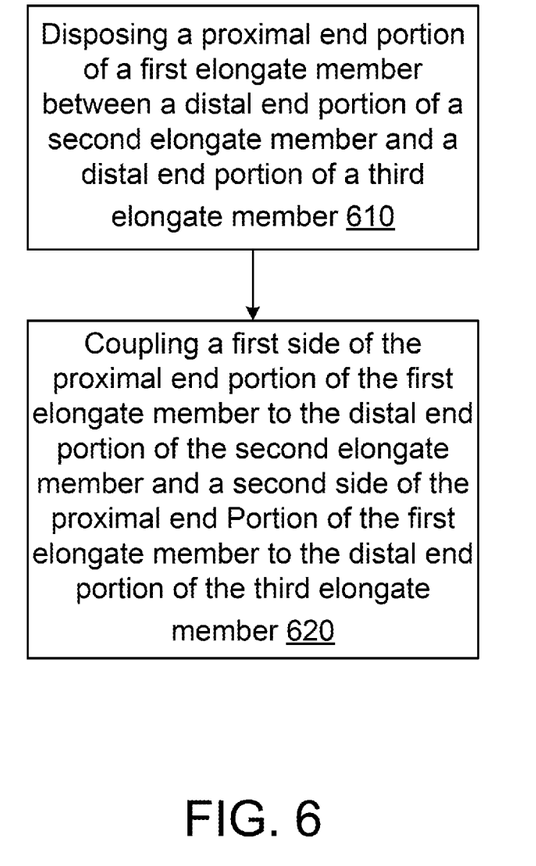
FIG. 6 is a diagram that illustrates a method for manufacturing a medical device according to an embodiment.

FIG. 6 is a diagram that illustrates a method for manufacturing a medical device according to an embodiment. In some embodiments, the method described in FIG. 6 can be used to produce, for example, the medical device 100 shown in FIG. 1.

As shown in FIG. 6, a proximal end portion of a first elongate member is disposed between a distal end portion of a second elongate member and a distal end portion of a third elongate member (block 610). In some embodiments, the first elongate member can be made of a material different from a material used to make the second elongate member and/or the third elongate member.

A first side of the proximal end portion of the first elongate member is coupled to the distal end portion of the second elongate member and a second side of the proximal end portion of the first elongate member is coupled to the distal end portion of the third elongate member (block 620). In some embodiments, the coupling of the first side of proximal end of the first elongate member to the distal portion of the second elongate member and the coupling of second side of the proximal end of the first elongate member to the distal end portion of the third elongate member can be performed using one or more attachment elements such as sutures, mechanical fasteners, adhesives, and/or so forth. In some embodiments, the proximal end portion of the first elongate member, the distal end portion of the second elongate member, and the distal end portion of the third elongate member can collectively define a layered portion of the medical device.

In some embodiments, the layered portion of the medical device can have a different configuration such as that shown in FIG. 3B. In such embodiments, the method of manufacturing can be adapted to produce the layered portion of the medical device by coupling the elongate members in a different order.

Figure 7:
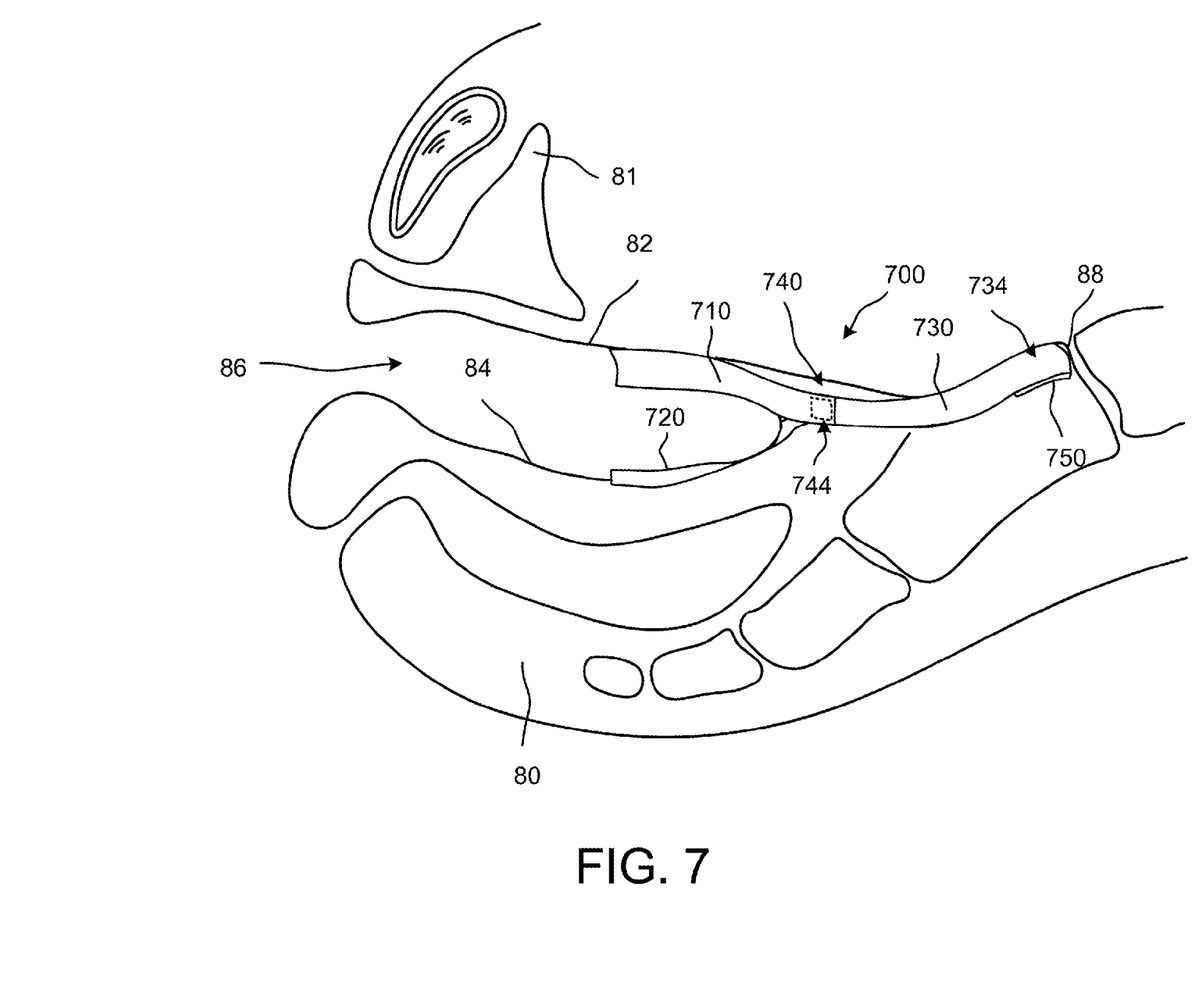
FIG. 7 illustrates placement of the medical device within a body of a patient.

FIG. 7 illustrates placement of the medical device 700 within a body of a patient. The medical device 700 is used hereafter to describe the placement within the body. However, other medical devices such as the medical device 100 shown in FIG. 1 may also be employed. The body portions of the patient such as an anterior vaginal wall 82, a posterior vaginal wall 84, a vagina 86, a sacrum 88, buttocks 80, and a bladder 81 are also illustrated in FIG. 7.

Figure 8:
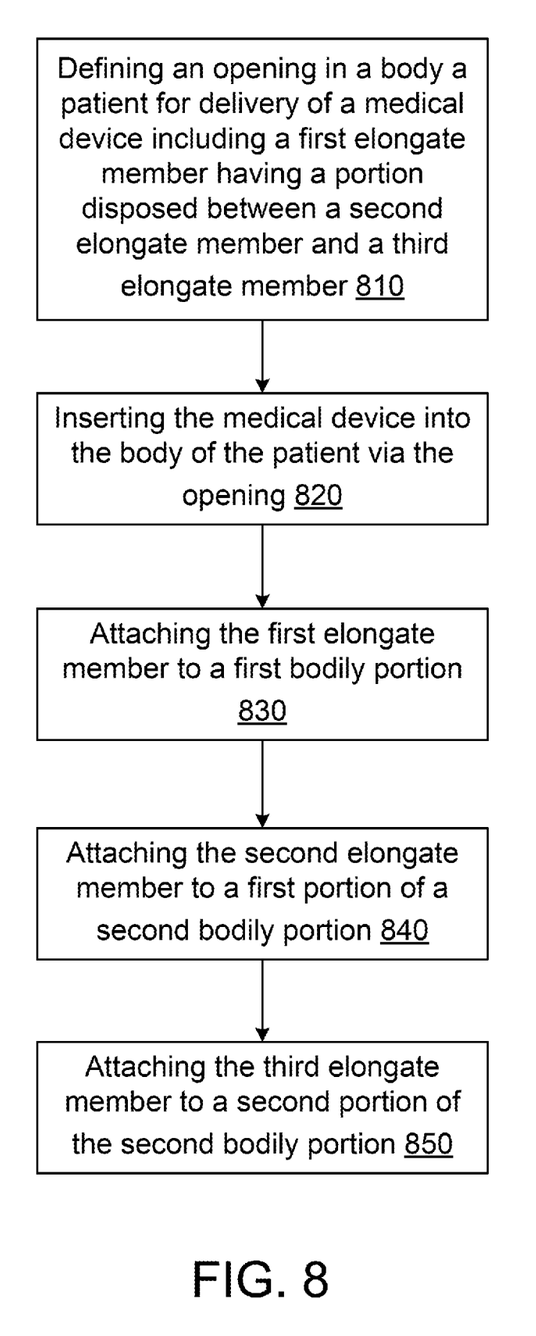
FIG. 8 is a flowchart illustrating a method of placement of a medical device, according to an embodiment.

As shown in FIG. 8, a first elongate member 710 is attached to an exterior surface of the anterior vaginal wall 82 and a second elongate member 720 is attached to an exterior surface of the posterior vaginal wall 84. A distal end portion 734 of the third elongate member 730 is attached to the sacrum 88 of the patient. In some other embodiments, the distal end portion 734 of the third elongate member 730 can be attached to another location in close proximity to the sacrum 88 (such as to bodily tissue proximate the sacrum 88). In some embodiments, the third elongate member 730 is made of a synthetic material such as polypropylene, and the first elongate member 710 and the second elongate member 720 are made of a biologic material such as bovine dermis, porcine dermis, and the like as discussed in conjunction with, for example, FIG. 1. In other embodiments, the third elongate member 730 is made of biologic material. In other embodiments, the first elongate member 710 and/or the second elongate member 720 are made a synthetic material.

As shown in FIG. 7, the medical device 700 includes a layered portion 740. In this embodiment, the layered portion includes sutures 744 configured to fixedly couple the elongate member 710, 720, and 730 that are included in the layered portion 740. Although not shown in FIG. 7, in some embodiments, the medical device 700 can include one or more placement features such as those shown in FIG. 4B.

In this embodiment, a fourth elongate member 750 (which can be made of a biologic material and/or a synthetic material) is optionally attached to the distal end portion 734 of the third elongate member 730. The fourth elongate member 750 is configured to be attached to the sacrum 88 of the patient. In other embodiments, the fourth elongate member 750 can be attached to another location in relatively close proximity to the sacrum 88 (such as to bodily tissue proximate the sacrum 88). In some embodiments, the fourth elongate member 750 is attached to the third elongate member 730 separately by an operator before implanting the medical device 700 into the body of the patient. In other embodiments, the fourth elongate member 750 can form as a part of the medical device 700 such that the operator can use the medical device 700 as such without separately attaching the fourth elongate member 750.

FIG. 8 is a flowchart illustrating a method of placement of a medical device, according to an embodiment. In some embodiments, the method illustrated in FIG. 8 can be used to place one or more of the medical devices described above (e.g., medical device 100 shown in FIG. 1).

An opening (e.g. an incision) is defined (e.g., created) in a body of a patient for delivery of a medical device including a first elongate member having a portion disposed between a second elongate member and a third elongate member (block 810). The medical device can be similar to one or more of the medical devices described above (e.g., medical device 100 shown in FIG. 1). In some embodiments, the opening can be an opening (e.g., an incision) within an abdomen or a vagina. In some embodiments, an operator/surgeon can make the opening laproscopically, laprotomically, or in another manner.

After the opening has been defined, the medical device can be inserted into the body of the patient via the opening (block 820). In some embodiments, the medical device can be inserted into the body of the patient using one or more medical tools such as a hemostat.

As shown in FIG. 8, the first elongate member is attached to a first bodily portion (block 830). In some embodiments, the first bodily portion can be, for example, the sacrum of the patient. In some embodiments, the first elongate member can be attached to the first bodily portion using one or more mechanical fasteners, adhesives, sutures, and/or so forth. In some embodiments, the first elongate member can be trimmed to a desirable length before being attached to the first bodily portion.

In this embodiment, the second elongate member is attached to a first portion of a second bodily portion (block 840), and the third elongate member is attached to a second portion of the second bodily portion (block 850). In some embodiments, the first portion of the second bodily portion is an anterior vaginal wall, and the second portion of the second bodily portion is a posterior vaginal wall. In some embodiments, the second elongate member and third elongate member are designed in shape and length in accordance with the anatomical structure of the coupling locations (where the elongate member is coupled/attached to the bodily tissues) at their respective vaginal walls. In some embodiments the second elongate member and the third elongate member are made of a biologic material. In some embodiments, the second elongate member and/or the third elongate member can be trimmed to a desirable length before being attached to second bodily portion.

In some embodiments, the order of operation described above can be modified. For example, the second elongate member can be attached to the first portion of the second bodily portion before the first elongate member is attached to the first bodily portion. Also, the third elongate member can be attached to the second portion of the second bodily portion before the first elongate member is attached to the first bodily portion.

In accordance with some embodiments, placement of the medical device may further include hydration of the biological material of one or more of the elongate members before delivery inside the body of the patient. In some embodiments, the elongate members can be made of biologic materials that are in a dry state before use (e.g., before use in a medical procedure) to maintain sterility. Sufficient hydration of the biologic material may performed to produce lubrication and tissue turgor during implantation. Hydration of the biologic material can enhance the malleability of the elongate members; therefore, the elongate members that are made of biologic material can be shaped according to the specific anatomical locations where they are attached upon hydration. In some embodiments, the elongate members made of biologic materials can be dipped in a saline solution for hydration.

In some embodiments, attachment of one or more of the elongate members to the bodily portions can be facilitated using one or more placement features. For example, the first elongate member can include a placement feature that can be used by a physician implanting the medical device into the body of the patient to align the first elongate member with one or more anatomical features within the body of the patient in a desirable fashion. As another example, the second elongate member can include a placement feature that can be used by a physician implanting the medical device into the body of the patient to align the second elongate member with the first portion of the second bodily portion in a desirable fashion.

In one general aspect, a medical device can include a first elongate member having a proximal end portion and a distal end portion. The proximal end portion of the first elongate member can be configured to be attached to a first portion of a bodily portion within a body of a patient. The medical device can include a second elongate member having a proximal end portion and a distal end portion where the proximal end portion of the second elongate member can be configured to be attached to a second portion of the bodily portion. The medical device can include a third elongate member having a proximal end portion. The proximal end portion can have a first side coupled to a surface of the distal end portion of the first elongate member and can have a second side coupled to a surface of the distal end portion of the second elongate member such that the proximal end portion of the first elongate member and the proximal end portion of the second elongate member are on a proximal end of the medical device opposite a distal end of the medical device including a distal edge of the third elongate member.

In some embodiments, at least one of the first elongate member or the second elongate member includes a biologic material, and the third elongate member includes a synthetic material. In some embodiments, the third elongate member is made of a material different from a material included in at least one of the first elongate member or the second elongate member. In some embodiments, the third elongate member has a flat, rectangular medial portion between the distal edge of the third elongate member and the proximal end portion of the third elongate member.

In some embodiments, the proximal end portion of the third elongate member is coupled to the distal end portion of the first elongate member and the distal end portion of the second elongate member via at least one suture piercing through the proximal end portion of the third elongate member, through the distal end portion of the first elongate member, and through the distal end portion of the second elongate member. In some embodiments, the proximal end portion of the third elongate member is coupled to the surface of the distal end portion of the first elongate member and to the surface of the distal end portion of the second elongate member by a suture including an x-shape pattern.

In some embodiments, the first side of the proximal end portion has a width approximately equal to a width of the surface of the distal end portion. In some embodiments, the first elongate member, the second elongate member, and the third elongate member each have a length greater than half of an overall length of the medical device. In some embodiments, the first elongate member, the second elongate member, and third elongate member are aligned along a longitudinal axis. In some embodiments, the third elongate member includes a placement feature aligned along a longitudinal axis of the third elongate member and configured to facilitate placement of the third elongate member into the body of the patient.

In some embodiments, at least one of the first elongate member or the second elongate member includes a plurality of openings configured as a visual guide to facilitate placement of the medical device into the body of the patient. In some embodiments, the medical device can also include a fourth elongate member made of a material included in at least one of the first elongate member, the second elongate member, or the third elongate member, the fourth elongate member coupled to the distal end portion of the third elongate member.

In another general aspect, a medical device can include a first elongate member made of a material and having a proximal end portion configured to be attached to a first portion of a bodily portion within a body of a patient where the first elongate member has a distal end portion. The medical device can include a second elongate member made of the material and having a proximal end portion configured to be attached to a second portion of the bodily portion where the first elongate member has a distal end portion. The medical device can also include a third elongate member having a proximal end portion in contact with and coupled to the distal end portion of the first elongate member and in contact with and coupled to the distal end portion of the second elongate member.

In some embodiments, the third elongate member has a distal end portion configured to be attached to a sacrum of the patient. In some embodiments, the first portion of the bodily portion is an anterior vaginal wall, and the second portion of the bodily portion is a posterior vaginal wall. In some embodiments, the third elongate member is fixedly coupled to the distal end portion of the first elongate member and fixedly coupled to the distal end portion of the second elongate member via a set of sutures such that the proximal end portion of the third elongate member is disposed between the distal end portion of the first elongate member and the distal end portion of the second elongate member.

In some embodiments, the first elongate member has a length substantially equal to a length of the second elongate member. In some embodiments, the material includes a biologic material, the third elongate member is made of a synthetic material. In some embodiments, the biologic material includes at least one of a bovine dermis, a porcine dermis, a cellulose based product, an allograft, or a cadaveric tissue. In some embodiments, at least one of the first elongate member, the second elongate member, or the third elongate member is made of a polypropylene material. In some embodiments, the material is a Xenograft material.

In yet another general aspect, a method can include disposing a proximal end portion of a first elongate member between a distal end portion of a second elongate member and a distal end portion of a third elongate member such that the second elongate member and the third elongate member are aligned along a longitudinal axis of the first elongate member. The second elongate member can have a proximal end portion configured to be attached to a first portion of a bodily portion within a body of patient, and the third elongate member can have a proximal end portion configured to be attached to a second portion of the bodily portion. The method can also include coupling a first side of the proximal end portion of the first elongate member to the distal end portion of the second elongate member and a second side of the proximal end portion of the first elongate member to the distal end portion of the third elongate member where the first elongate member is made of a material different than at least one of the second elongate member or the third elongate member.

In some embodiments, the at least one of the second elongate member or the third elongate member includes a biologic material where the third elongate member includes a synthetic material. In some embodiments, the coupling includes fixedly coupling via a set of sutures. In some embodiments, the method can include forming a placement feature along at least one of the first elongate member, the second elongate member, or the third elongate member.

Detailed embodiments are disclosed herein; however, it is to be understood that the disclosed embodiments are merely exemplary embodiments, which may be implemented in various forms. Therefore, specific structural and functional details disclosed herein are to be interpreted as non-limiting, and as a basis for the claims and as a representative. In other words, while the disclosure includes preferred embodiments shown and described in detail, various modifications and improvements thereon will become readily apparent to those skilled in the art. Any portion of the apparatus and/or methods described herein may be combined in any combination, except mutually exclusive combinations. The embodiments described herein can include various combinations and/or sub-combinations of the functions, components and/or features of the different embodiments described. Further, the terms and phrases used herein are not intended to be limiting, but to provide an understandable description of the invention. Accordingly, the spirit and scope of the present embodiments, are not to be limited by the foregoing examples, but it is to be understood in the broadest sense permitted.

What is claimed is:

1. A medical device, comprising:
a first elongate member having a proximal end portion and a distal end portion, the proximal end portion of the first elongate member configured to be attached to a first portion of a bodily portion within a body of a patient;
a second elongate member having a proximal end portion and a distal end portion, the proximal end portion of the second elongate member configured to be attached to a second portion of the bodily portion; and
a third elongate member having a proximal end portion, the proximal end portion of the third elongate member having a first side coupled to a surface of the distal end portion of the first elongate member,
the proximal end portion of the third elongate member having a second side coupled to a surface of the distal end portion of the second elongate member,
wherein the proximal end portion of the first elongate member and the proximal end portion of the second elongate member are on a proximal end of the medical device opposite a distal end of the medical device including a distal edge of the third elongate member,
wherein portions of the first, second, and third elongate members define a layered portion having at least three layers, and the at least three layers are coupled together via one or more sutures.

2. The medical device of claim 1, wherein the first elongate member and the second elongate member include a biologic material, and the third elongate member includes a synthetic material such that the layered portion includes a biologic-synthetic-biologic layered structure.

3. The medical device of claim 1, wherein the one or more sutures include a first set of sutures coupling two layers of the layered portion together including the distal end portion of the first elongate member and the proximal end portion of the third elongate portion, and a second set of sutures coupling the two layers to the distal end portion of the second elongate member.

4. The medical device of claim 1, wherein the third elongate member has a flat, rectangular medial portion between the distal edge of the third elongate member and the proximal end portion of the third elongate member.

5. The medical device of claim 1, wherein the one or more sutures include at least one suture piercing through all layers of the layered portion including through the proximal end portion of the third elongate member, through the distal end portion of the first elongate member, and through the distal end portion of the second elongate member.

6. The medical device of claim 1, wherein the proximal end portion of the third elongate member is coupled to the surface of the distal end portion of the first elongate member and to the surface of the distal end portion of the second elongate member by the one or more sutures configured as an x-shape pattern.

7. The medical device of claim 1, wherein the first side of the proximal end portion of the third elongate member has a width approximately equal to a width of the surface of the distal end portion of the first elongate member.

8. The medical device of claim 1, wherein the first elongate member, the second elongate member, and the third elongate member each have a length greater than half of an overall length of the medical device.

9. The medical device of claim 1, wherein the proximal end portion of third elongate member overlaps with the distal end portion of the first elongate member by a first distance, and the proximal end portion of the third elongate member overlaps with the distal end portion of the second elongate member by a second distance, the first distance being greater than the second distance.

10. The medical device of claim 1, wherein the third elongate member includes a placement feature aligned along a longitudinal axis of the third elongate member and configured to facilitate placement of the third elongate member into the body of the patient.

11. The medical device of claim 1, wherein at least one of the first elongate member and the second elongate member includes a plurality of openings configured as a visual guide to facilitate placement of the medical device into the body of the patient.

12. The medical device of claim 1, further comprising:
a fourth elongate member made of a material included in at least one of the first elongate member, the second elongate member, and the third elongate member, the fourth elongate member being coupled to the distal end portion of the third elongate member.

13. A medical device, comprising:
a first elongate member made of a material and having a proximal end portion configured to be attached to a first portion of a bodily portion within a body of a patient, the first elongate member having a distal end portion;
a second elongate member made of the material and having a proximal end portion configured to be attached to a second portion of the bodily portion, the second elongate member having a distal end portion; and
a third elongate member having a proximal end portion in contact with and coupled to the distal end portion of the first elongate member such that the proximal end portion of the third elongate member overlaps with the distal end portion of the first elongate member by a first distance, the proximal end portion of the third elongate member in contact with and coupled to the distal end portion of the second elongate member such that the proximal end portion of the third elongate member overlaps with the distal end portion of the second elongate member by a second distance,
wherein overlapping portions of the first, second, and third elongate members define a layered portion having at least three layers, and the at least three layers are coupled together via a set of sutures.

14. The medical device of claim 13, wherein the third elongate member has a distal end portion configured to be attached to a sacrum of the patient.

15. The medical device of claim 13, wherein the first portion of the bodily portion is an anterior vaginal wall, and the second portion of the bodily portion is a posterior vaginal wall.

16. The medical device of claim 13, wherein the third elongate member is fixedly coupled to the distal end portion of the first elongate member and fixedly coupled to the distal end portion of the second elongate member via the set of sutures such that the proximal end portion of the third elongate member is disposed between the distal end portion of the first elongate member and the distal end portion of the second elongate member.

17. The medical device of claim 13, wherein the first elongate member has a length substantially equal to a length of the second elongate member.

18. The medical device of claim 13, wherein at least one of the first elongate member, the second elongate member, and the third elongate member is made of a polypropylene material.

19. The medical device of claim 13, wherein the material of both the first elongate member and the second elongate member is a Xenograft material, and the third elongate member is made of a polyropylene material.

20. A method, comprising:
disposing a proximal end portion of a first elongate member between a distal end portion of a second elongate member and a distal end portion of a third elongate member such that the second elongate member and the third elongate member are aligned along a longitudinal axis of the first elongate member,
the second elongate member having a proximal end portion configured to be attached to a first portion of a bodily portion within a body of a patient, the third elongate member having a proximal end portion configured to be attached to a second portion of the bodily portion;
coupling a first side of the proximal end portion of the first elongate member to the distal end portion of the second elongate member such that the proximal end portion of the first elongate member overlaps with the distal end portion of the second elongate member by a first distance; and
coupling a second side of the proximal end portion of the first elongate member to the distal end portion of the third elongate member such that the proximal end portion of the first elongate member overlaps with the distal end portion of the third elongate member by a second distance,
wherein overlapping portions of the first, second, and third elongate members define a layered portion having at least three layers, and the at least three layers are coupled together via one or more sutures,
wherein the first elongate member includes a synthetic material, and the second and third elongate members include a biologic material such that the layered portion is a biologic-synthetic-biologic layered structure.

* * * * *